United States Patent [19]

Niedrach et al.

[11] 3,957,612

[45] May 18, 1976

[54] IN VIVO SPECIFIC ION SENSOR

[75] Inventors: Leonard W. Niedrach; Oliver H. LeBlanc, Jr., both of Schenectady, N.Y.

[73] Assignee: General Electric Company, Schenectady, N.Y.

[22] Filed: July 24, 1974

[21] Appl. No.: 491,605

[52] U.S. Cl............................ 204/195 M; 204/195 P
[51] Int. Cl.².......................................... G01N 27/46
[58] Field of Search............ 204/1 T, 195 R, 195 F, 204/195 M, 195 P, 195 G, 195 L

[56] References Cited
UNITED STATES PATENTS

| | | | |
|---|---|---|---|
| 3,498,899 | 3/1970 | Kater et al........................ | 204/195 F |
| 3,673,069 | 6/1972 | Niedrach et al.................. | 204/195 P |
| 3,691,047 | 9/1972 | Ross et al....................... | 204/195 M |
| 3,705,089 | 12/1972 | Grubb............................. | 204/195 F |
| 3,709,810 | 1/1973 | Grubb et al..................... | 204/195 R |
| 3,718,569 | 2/1973 | Petersen et al.................. | 204/195 G |
| 3,743,588 | 7/1973 | Brown et al..................... | 204/195 M |
| 3,767,553 | 10/1973 | Brown et al..................... | 204/195 M |

*Primary Examiner*—T. Jung
*Attorney, Agent, or Firm*—Charles T. Watts; Joseph T. Cohen; Jerome C. Squillaro

[57] ABSTRACT

An in vivo specific ion sensor contains a specific ion electrode and surrounding reference half cell which has its immobilized electrolyte adjacent to and spaced from the specific ion electrode. The specific ion sensor is introduced, for example, into the blood stream by passing it through a cannula which perforates the subject's tissue and the underlying wall of the blood vessel.

2 Claims, 3 Drawing Figures

IN VIVO SPECIFIC ION SENSOR

This invention relates to a specific ion sensor and, more particularly, to an ion specific sensor for in vivo application.

Sensors are employed to determine the content of a specific substance in a fluid or atmosphere. For example, a sensor might be employed to determine the hydrogen ion activity or pH, the oxygen content or carbon dioxide content in a sample.

For in vitro applications, specific ion sensors are known in the prior art for measuring the hydrogen ion activity or pH of a sample. Such a sensor employs a reference electrode and a sensing electrode, such as a glass electrode immersed in a solution, whereby the potential difference between the two electrodes is a function of the concentration of the hydrogen ion in the solution. The salt bridge reference electrode is the most useful. This contains an electrochemically active metallic element in contact with an intermediate, or bridge, salt solution, which separates the metallic element from the sample solution to be measured. Electrical connection between the salt bridge solution and the sample solution is made generally by a liquid contact through an aperture referred to as a liquid junction. Such sensors which are made of glass employ separate spaced apart reference electrodes and sensing electrodes or employ a glass sensing electrode surrounded by a reference electrode making a suitable junction with the solution being examined.

In U.S. Pat. No. 3,709,810 there is described and claimed a hydrogen ion selective sensor for particular application as an in vivo sensor. This sensor, which does not employ glass electrodes, has a hydrogen ion selective electrode at one end of an elongated insulating wire which is surrounded by a chamber containing a reference electrode and a reference electrolyte. A wick is provided from the interior of the reference electrolyte chamber to the exterior surface of the sensor to provide an electrolyte bridge. In U.S. Pat. No. 3,705,089 there is described and claimed a reference electrode half cell. This half cell includes an elongated tube of electrically insulating material containing a reference electrode and a gelled reference electrolyte. Both of these patents are assigned to the same assignee as the present application.

Our present invention is directed to an improved miniaturized specific ion sensor for in vivo application. As opposed to the above first mentioned prior art, the subject invention eliminates glass electrodes and provides a miniature structure for in vivo application. As opposed to the prior art disclosed in the above-mentioned patents, the present application provides an improved sensor with an immobilized electrolyte which eliminates the wick arrangement described in the first of the above two patents. As opposed to the second above described patent, the present invention is directed to a sensor rather than to a reference electrode half cell.

The primary objects of our invention are to provide a rugged, accurate and miniaturized sensor for in vivo applications.

In accordance with one aspect of our invention, an in vivo specific ion sensor contains a specific ion electrode and surrounding reference half cell which has its immobilized electrolyte adjacent to and spaced from the specific ion electrode.

These and various other objects, features and advantages of the invention will be better understood from the following description taken in connection with the accompanying drawing in which.

Figure 1:
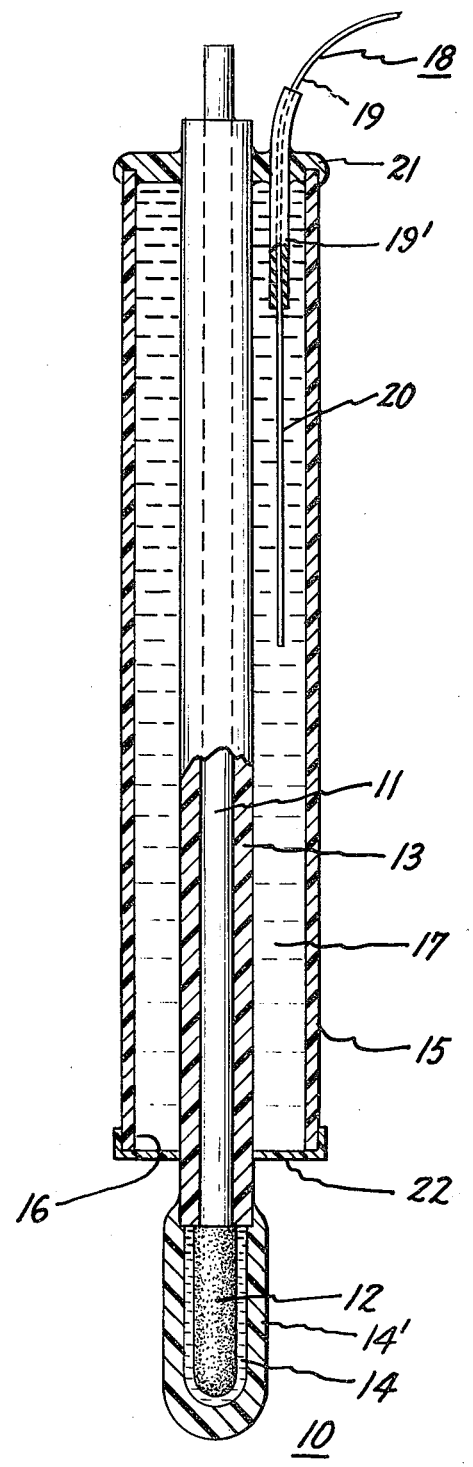
FIG. 1 is a sectional view of an in vivo specific ion sensor made in accordance with our invention.

In FIG. 1 of the drawing, there is shown generally at 10 an in vivo specific ion sensor made in accordance with our invention. Sensor 10 is shown in the form of a flexible metallic elongated electrode lead 11 which is electronically conducting and has an electrochemically active portion 12 at one end thereof. Electrical insulation 13 surrounds and adheres to electrode lead 11. An immobilized electrolyte 14 coats electrochemically active portion 12. A membrane barrier 14' selectively permeable to a particular ionic species encapsulates electrolyte 14 and electrochemically active portion 12 and overlaps and bonds to insulation 13. Portion 12, electrolyte 14 and membrane barrier 14' form an electrochemically active region at the end of lead 11. Electrolyte 14 contains at least an ion that enters into electrochemical equilibrium with electrochemically active portion 12, as well as the ion to which membrane barrier 14' is selectively permeable. Tube 15, which is electrically insulating, surrounds at least a portion of electrode lead 11 and its associated insulation 13. One end 16 of tube 15 is adjacent to and spaced from barrier 14'. An immobilized aqueous electrolyte 17 is contained within tube 15. A metallic element 18 partially within tube 15 comprises a metallic electrode lead 19 partially coated with insulation 19' and on which at least a portion thereof there is an electrochemically active region 20 that can enter into electrochemical equilibrium with an ion in electrolyte 17. Electrode lead 19 extends externally of tube 15 through a seal 21 closing the opposite end of tube 15. An ion-permeable membrane barrier 22 is shown closing end 16 of tube 15. The purpose of this membrane barrier 22 is to impede the transport of living cells, or of protein molecules, into electrolyte 17 when the sensor is immersed in a solution, such as blood, which contains such cells and molecules. At the same time it must permit ready transport of small electrolyte ions. Therefore, the membrane serves a function similar to that of membranes commonly used for dialysis and can therefore be constructed of materials used for dialysis membranes, such as cellulose acetate, for example. Such a membrane barrier 22 is not critical.

Figure 2:
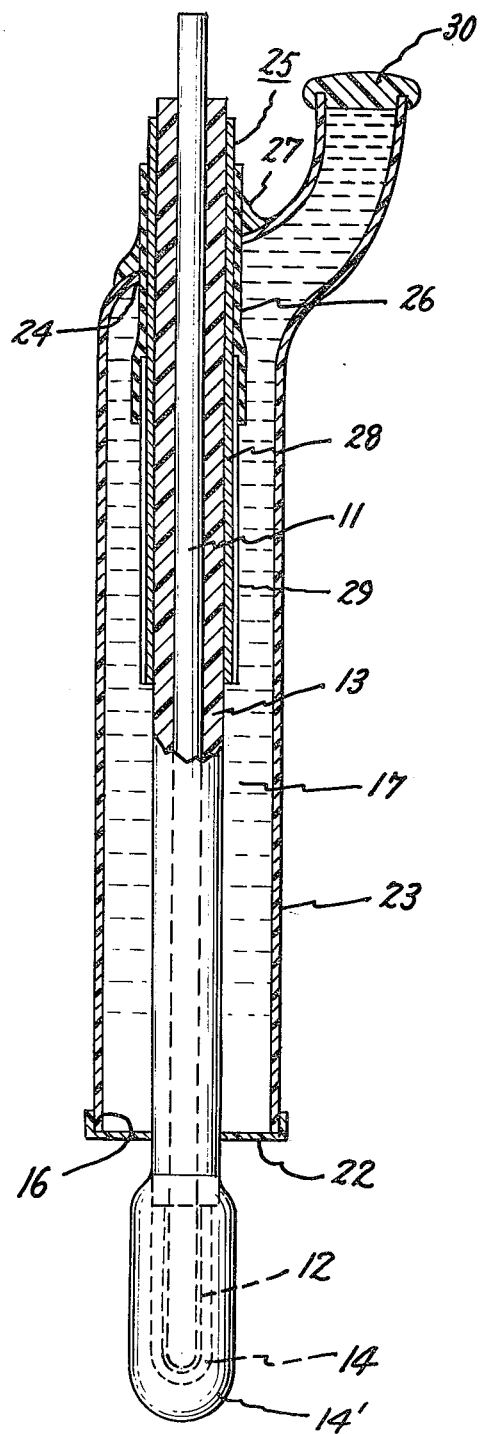
FIG. 2 is a sectional view of a modified in vivo specific ion sensor.

In FIG. 2 of the drawing, there is shown a modified in vivo specific ion sensor. The sensor is shown in the form of a flexible metallic elongated electrode lead 11 which is electronically conductive and has an electrochemically active portion 12 adjacent one end thereof. Electrical insulation 13 surrounds and adheres to electrode lead 11. Immobilized electrolyte 14 coats electrochemically active portion 12. Membrane barrier 14' selectively permeable to a particular ionic species encapsulates electrolyte 14 and electrochemically active portion 12 and overlaps and bonds to insulation 13. An irregularly curved, electrically insulating tube 23 surrounds at least a portion of electrode lead 11 and its associated insulation 13. One end 16 of tube 23 is adjacent to and spaced from barrier 14'. An aperture 24 is positioned in tube 23. A portion of the electrode lead 11, adhering insulation 13 and a portion of a metallic element 25 partially coated with insulation 26 extend outwardly through aperture 24. A seal 27 is provided between metallic element 25 and tube 23. A portion of metallic element 25 within tube 23 comprises a metallic electrode lead 28 and an electrochemically active region 29 that can enter into electrochemical equilibrium with an ion in electrolyte 17. An immobilized aqueous electrolyte 17 is within tube 23 and contacts active region 29 of metallic element 25. A seal 30 closes the opposite end of tube 23. An ion-permeable membrane barrier 22 closes end 16 of tube 23. Membrane 22 is not critical.

Figure 3:
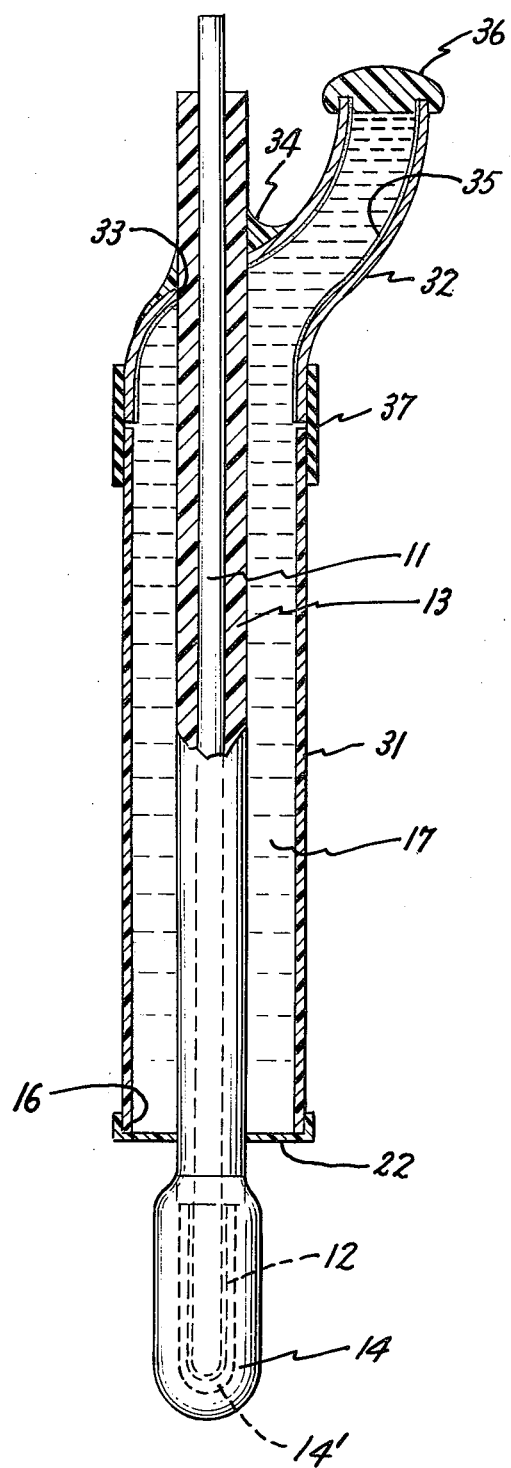
FIG. 3 is a sectional view of a further modified in vivo sensor.

In FIG. 3 of the drawing, there is shown a further modified in vivo specific ion sensor. The sensor is shown in the form of a flexible metallic elongated electrode lead 11 which is electronically conductive and has an electrochemically active portion 12 adjacent one end thereof. Electrical insulation 13 surrounds and adheres to electrode lead 11. Immobilized electrolyte 14 coats electrochemically active portion 12. Membrane barrier 14' encapsulates electrolyte 14 and active portion 12. An electrically insulating tube 31 surrounds at least a portion of electrode lead 11. One end 16 of tube 31 is adjacent to and spaced from barrier 14'. An irregularly curved metallic tube 32 is in contact with the other end of electrically insulating tube 31. An aperture 33 is positioned in metallic tube 32. A portion of electrode lead 11 and adhering insulation 13 extends outwardly through aperture 33. A seal 34 is provided between insulation 13 and metallic tube 32. An immobilized aqueous electrolyte 17 is contained within both tubes 31 and 32. An electrochemically active region 35 is contained on at least a portion of the inner surface of metallic tube 32. A seal 36 closes the opposite end of the metallic tube 32. An ion-permeable membrane barrier 22 closes end 16 of tube 31. Membrane barrier 22 is not critical. A rubber sleeve 37 is shown joining and sealing together tubes 31 and 32. Various other suitable means can be employed for joining these tubes together.

The specific ion electrode of the above in vivo sensor can be formed by a method of applying layers or elements by dipping or immersing the initial electrode lead in different solutions after which the solution solvent may be evaporated. The application of layers is preferably accomplished by immersion steps but other suitable means include coating, spraying, brushing, etc. The use of immersion steps is described and claimed in U.S. Pat. No. 3,798,750.

Our in vivo sensor can be formed by employing a flexible, metallic elongated electrode lead. In a first embodiment as shown in FIG. 1 and as described above, an electrochemically active portion of, for example, silver coated with a silver chloride is present at one end of the lead. The remaining portion of the lead except for the electrochemically active portion and for a short length at the opposite end is insulated with suitable electrical insulation, for example, epoxy resins, polyimides, polyethers, poly(tetrafluoroethylene), silicone rubber or poly(dimethylsiloxane)poly(bisphenol-A carbonate) block copolymers, or multiple coats of such insultions in order to provide improved bonding, for example, be a first coat of poly(tetrafluoroethylene) followed by a second coat of a poly(dimethylsiloxane)poly(bisphenol-A carbonate) block copolymer. The electrochemically active portion is coated with a layer of an immobilized aqueous electrolyte containing at least the ion which is to be detected and also an ion which enters into electrochemical equilibrium with the electrochemically active region of the lead, such as a chloride ion. The layer of immobilized electrolyte can be applied by dipping the end of the lead into a volume of such electrolyte. Then, over the layer of this immobilized electrolyte a polymer membrane selectively permeable to the ion to be sensed is applied, for example, by dipping the lead into a solution containing the polymer. The solvent of the latter solution is then evaporated to leave a film of the selectively permeable polymer covering the immobilized electrolyte and the electrochemically active region of the lead. The resulting structure is the ion-specific electrode of the sensor. The selectively permeable, polymer membrane barrier can, for example, be selectively permeable to hydrogen, potassium or calcium ions. The immobilized electrolyte must contain the ion to which the membrane is selectively permeable, and the ion which enters into electrochemical equilibrium with the active region of the metallic lead. For example, if the electrochemically active region of lead is silver and silver chloride and if the polymer membrane is selectively permeable to hydrogen ions, then a suitable immobilized electrolyte contains sodium chloride and a suitable hydrogen ion buffering electrolyte such as disodium hydrogen phosphate and potassium dihydrogen phosphate and a suitable gelling agent, such as 2% or 3% Methocel gel, a methylcellulose material sold by Dow Chemical Company, Midland, Michigan. Polymers selectively permeable to hydrogen ions are described and claimed in U.S. Pat. No. 3,743,588. Polymers selectively permeable to potassium ions are described and claimed in U.S. Pat. No. 3,767,553. Both of these patents are assigned to the same assignee as the present application. Both of these patents and the subject matter thereof are hereby incorporated by reference.

The tube which surrounds at least a portion of the electrode lead is an electrical insulator. The tube can be made from a variety of materials with various plastics being preferred. One end of the tube is adjacent to and spaced from the active region of the electrode lead. A metallic element, which comprises a metallic electrode lead and an electrochemically active region of silver and silver halide on at least a portion thereof is positioned in the tube in a variety of manners. The metallic element of the reference electrode lead extends outwardly from the tube for connection to an appropriate electrical circuit. An immobilized aqueous electrolyte is contained within the tube and is in contact with the active portion of the metallic element of the reference electrode. A suitable electrolyte is 0.15 molar sodium chloride which is immobilized with a conventional thickening or gelling agent, such as 2% agar-agar.

At the opposite end of the tube, the electrode lead with adhering insulation extends outwardly. A seal closes this end of the tube. Such a seal can be made of a variety of materials. An epoxy resin cement is a suitable seal material. Optionally, an ion-permeable membrane barrier can close the opposite end of the tube adjacent the active region. Such a barrier can be made, for example, of cellulose acetate. A high impedance electrometer is connected to the electrode leads of the sensor. The terminal voltage is read between the metallic lead of the ion-specific electrode and the metallic lead of the reference electrode. The terminal voltage from this sensor in operation will be a function of the pH. The sensor is introduced into the blood stream of a patient by passing it through a cannula which perforates the subject's tissue and the underlying wall of a blood vessel. When the sensor is in the blood stream, the specific ion active region and the open end of the tube are in communication with the blood. In this manner, the immobilized electrolyte within the tube forms an electrolytic bridge between the blood and the electrochemically active portion of the metallic element of the electrode.

In another embodiment of our in vivo sensor there is provided a modified tube which surrounds at least a portion of the electrode lead. This tube as in the first embodiment can be made from a variety of materials from various plastics such as polytetrafluoroethylene. The modified tube is an electrically curved configuration. An aperture is positioned in the tube so that a portion of the electrode lead and adhering insulation can extend outwardly through the aperture. The aperture is positioned so that the electrode lead is aligned axially within the tube. A seal made from a material such as epoxy resin cement is provided between the insulation and the tube to seal the structure together. A similar epoxy resin seal is provided to close the open end of the tube as in the first embodiment. As it is described above in FIG. 2, a metallic reference electrode element with a silver and silver halide region is provided around and adhering to the insulation surrounding the first electrode lead. With this configuration, a portion of the metallic reference electrode element extends outwardly from the tube through the aperture therein to form the reference electrode lead connection. It will, of course, be appreciated that a metallic element such as a wire with a silver and silver halide portion can be employed in contact with the electrolyte instead. The metallic reference electrode lead can then be extended outwardly from the tube through either seal.

A further embodiment of our in vivo sensor has a modified tube as shown in FIG. 3 and described above. This modified tube has a first plastic portion similar in construction to the earlier embodiments. An irregularly curved silver tube 32 is sealed to the upper end of the plastic tube and is provided with an aperture 33 through which the first electrode lead and adhering insulation extends outwardly from the tube structure. Various methods of sealing the tubes together can be employed. A simplified arrangement is a rubber sleeve 37 positioned over the exterior surface of both tubes and surrounding the joint therebetween. As in the previous embodiment, a seal is provided thereby sealing the insulation adhering to the first electrode lead and the silver tube. A seal 36 is also provided at the initial open end of the silver tube. The interior surface of the silver tube 32 or at least a portion of the interior surface of such tube is coated with silver halide 35 to provide the metallic element of the reference electrode. The two previous embodiments with an irregular curved tube structure and an initial aperture therein produce an in vivo sensor which has a rugged structure pvodied by the sealing and support of the first electrode lead by the tube.

Examples of an in vivo sensor made in accordance with our invention are as follows:

Example I

An in vivo pH sensor was formed in accordance with the above description and is generally shown in FIGS. 1 and 2 of the drawing. A first flexible metallic elongated electrode was provided in the form of a 0.015 inch diameter silver wire insulated with a first layer of poly(tetrafluoroethylene) and a second layer of poly(siloxane)poly(bisphenol-A carbonate) block copolymer, except for a short, 1 cm length at either end. A layer of silver chloride was applied to the uninsulated silver at one end of the lead by electrolytic anodization for 5 minutes at 0.6 milliamperes current in 0.1 molal sodium chloride. A thin layer of an immobilized electrolyte was then applied over the silver chloride by dipping the end of the lead in a large volume of the electrolyte, then rapidly removing it. The composition of this immobilized electrolyte was as follows: 0.080 molar disodium hydrogen phosphate, 0.083 molar potassium dihydrogen phosphate, and three weight percent methylcellulose, all dissolved in water. A sheath of a polymer selectively permeable to $H^+$ ions was then applied over the immobilized electrolyte layer, and overlapped a portion of the insulation of the elongated silver lead, by dipping into a solution of this polymer formulation in methylene chloride, then removing the methylene chloride solvent by drying for one minute in dry nitrogen gas, then drying for ten minutes more in air. The polymer selectively permeable to $H^+$ ions was of the type described and claimed in U.S. Pat. No. 3,743,588 referred to above. This completed the fabrication of the pH-sensitive element of the sensor.

The fabrication of the whole sensor was completed by incorporating the pH-sensitive element into a structure with a reference electrode as shown generally in FIG. 2 except that the silver-silver chloride wire is of the type shown in FIG. 1. A 0.055 inch hole was drilled at the appropriate position in the wall of a length of poly(tetrafluoroethylene) tubing. The pH-sensitive element was inserted into this tube, as shown in FIG. 2, so that the end of its silver lead passed through the hole in the tube. Then a 0.005 inch diameter silver wire was also inserted through the same hole in the tubing, as shown in FIGS. 1 and 2. A portion of one end of this 0.005 inch diameter silver wire had previously been coated with a layer of silver chloride by electrolytic annodization, by the same general procedure described above, and this end of the wire was the end placed within the lumen of the poly(tetrafluoroethylene) tube. The hole in the tube was then sealed with epoxy resin, thereby bonding together the tube, the 0.005 inch diameter silver wire, and the pH-sensitive element constructed on the elongated, insulated 0.015 inch diameter silver wire. The lumen of the poly(tetrafluoroethylene) tube was then filled with an immobilized aqueous electrolyte solution by injecting this solution through the remaining free end of the tubing by means of a hypodermic syringe. The composition of this immobilized electrolyte solution was as follows: 0.113 molar disodiumhydrogenphosphate, 0.005 molar potassiumdihydrogenphosphate, and 2 percent by weight agar-agar. Next the free end of the poly(tetrafluoroethylene) tube was crimped by means of a hot tool, then sealed with epoxy resin. This completed the fabrication of a complete pH sensor of a structure as shown generally in FIG. 2.

Example II

The in vivo pH sensor made as described in Example I was tested at 25°C by immersing it in aqueous electrolyte solutions of different pH and measuring the electrical potential difference between the 0.015 inch diameter silver wire, which formed the electrical connection to the pH-sensitive element of the sensor, and the 0.005 inch diameter silver wire, which formed the electrical connection to the reference element of the sensor. The results obtained are listed in Table I. In column one is listed the pH of the test solution as determined with a calibrated glass pH electrode. In column two is listed the sensor potential difference found. A comparison of the data in these first two columns shows that the mathematical relationship between the sensor potential and the pH of the external solution is best described, given the experimental error, as a linear one. Hence, measurement of the sensor potential at any two pH values serves to calibrate the sensor, so that any other value of potential than one should measure can be expressed immediately as the pH indicated by the sensor. Such data are shown in column three of Table I, where the first two entries were the values used for the linear calibration.

TABLE I

| Actual Solution pH | Sensor Potential (millivolts) | Indicated Solution pH |
|---|---|---|
| 6.134 | −23.0 | (6.134) |
| 7.927 | −129.2 | (7.927) |
| 7.302 | −92.2 | 7.302 |
| 6.127 | −24.7 | 6.162 |
| 7.055 | −73.8 | 6.992 |
| 6.485 | −42.2 | 6.458 |

While other modifications of the invention and variations thereof which may be embraced within the scope of the invention have not been described, the invention is intended to include such as may be embraced within the following claims.

What we claim as new and desire to secure by Letters Patent of the United States is:

1. An in vivo specific ion sensor which comprises a flexible metallic elongated electrode lead, an electrochemically active portion at one end thereof, a first immobilized electrolyte coating the electrochemically active portion, a membrane barrier selectively permeable to a particular ionic species encapsulating the electrochemically active portion and the electrolyte, electrical insulation surrounding and adhering to the electrode lead, an electrically-insulating irregularly-curved tube surrounding at least a portion of the electrode lead and electrically insulated therefrom, one end of the tube being disposed adjacent to and spaced from the membrane barrier and being closed by a second ion-permeable membrane, an aperture in the tube, a second immobilized electrolyte contained within the tube and in contact with the second ion-permeable membrane, a metallic reference electrode element partially within the tube comprising a metallic electrode lead and an electrochemically active region, the active region of the reference electrode being in contact with the second electrolyte, a portion of the metallic reference electrode element extending externally of the tube through the tube aperture, a seal closing the aperture around the reference electrode, and a seal closing the opposite end of the tube.

2. An in vivo specific ion sensor which comprises a flexible metallic elongated electrode lead, an electrochemically active portion at one end thereof, a first immobilized electrolyte coating the electrochemically active portion, a membrane barrier selectively permeable to a particular ionic species encapsulating the electrochemically active portion and the electrolyte, electrical insulation surrounding and adhering to the electrode lead, a tube of electrically-insulating material surrounding at least a portion of the electrode lead and electrically insulated therefrom, one end of the tube being disposed adjacent to and spaced from the membrane barrier and being closed by a second ion-permeable membrane, a second immobilized electrolyte contained within the tube and in contact with the second ion-permeable membrane, an irregularly-curved metallic tube having one end sealed to the open end of the electrically-insulating tube and having an aperture to receive the electrode lead and adhering electrical insulation, an electrochemically active region on at least a portion of the inner surface of the metallic tube and in contact with the second electrolyte, a seal closing the aperture around the electrode lead, and a seal closing the other end of the metallic tube.

* * * * *